United States Patent [19]
Kolich et al.

[11] 3,996,312
[45] Dec. 7, 1976

[54] HALOPHENOXYPHOSPHAZENE FIRE RETARDANTS

[75] Inventors: Charles H. Kolich, Northville; Henry G. Braxton, Jr., Franklin; Urho A. Lehikoinen, Detroit, all of Mich.

[73] Assignee: Ethyl Corporation, Richmond, Va.

[22] Filed: Nov. 21, 1974

[21] Appl. No.: 525,932

[52] U.S. Cl. ............................ 260/927 N; 260/45.7 P
[51] Int. Cl.² ........................ C07C 9/06; C08K 5/53
[58] Field of Search .............................. 260/927 N

[56] References Cited
UNITED STATES PATENTS

| | | | |
|---|---|---|---|
| 3,206,494 | 9/1965 | Lund et al. | 260/927 N |
| 3,419,504 | 12/1968 | Klender | 260/927 N |
| 3,795,526 | 3/1974 | Bergeron | 260/927 N X |

*Primary Examiner*—Anton H. Sutto
*Attorney, Agent, or Firm*—Donald L. Johnson; John F. Sieberth; Robert A. Linn

[57] ABSTRACT

The fire retardancy of polyesters is enhanced with halophenoxyphosphazenes that contain a P—O—P bond. Preferred materials are reaction products of a halogenated phenol and a phosphonitrilic halide. Brominated phenols are preferred although chlorophenols can be used. Of the brominated phenols, preferred starting materials are p-bromophenol, 2,4-dibromophenol and mixtures thereof. Phosphonitrilic chlorides are preferred starting materials. Pure phosphonitrilic halides can be used; however, phosphonitrilic halide mixtures are preferred because of their availability. Cyclic and linear phosphonitrilic halides are useful as well as mixtures thereof. Saturated and unsaturated polyesters can be made fire retardant by this invention, as can thermoplastic and thermosetting materials. Linear and cross-linked polyesters can be treated. Preferred polyesters are fiber-forming polyesters of a diol and dibasic acid, such as poly(ethylene terephthalate) and poly(1,4-cyclohexylenedimethyleneterephthalate).

3 Claims, No Drawings

HALOPHENOXYPHOSPHAZENE FIRE RETARDANTS

BACKGROUND OF THE INVENTION

Phosphazenes and their preparation are disclosed in U.S. Pat. No. 2,109,491. Partially substituted materials are mentioned in U.S. Pat. No. 3,206,494. p-Bromophenoxyphosphazenes are known, Dell et al, *J. Chem. Soc.* 4070 (1965). High molecular weight poly)-phenoxyphosphazene) has been described; Kugel et al, *Inorganic Chem.* 5, 1709 (1966).

Phosphonitrilic halides can be prepared by reacting NH$_4$Cl with PCl$_5$; Emsley et al, *J. Chem. Soc.* (A), 768 (1971). Other references dealing with this preparation are cited therein and mentioned below.

Phosphonitrilic polymers containing P—O—P bonds are disclosed on pages 97-98 of *Chemical Week*, Feb. 20, 1965. Such polymers are also disclosed in U.S. Pat. No. 3,459,838.

Fire retardant use of phosphazenes with P—O—P bonds, and which also contain aryloxy groups, is disclosed in German Pat. No. 2,306,510. The compounds are made by reacting a phosphonitrilate polymer with phosphonitrilic chloride, or PCl$_3$, POCl$_3$ or PSCl$_3$.

Various fire retardants have been suggested for polyesters; confer for example, U.S. Pat. Nos. 2,909,501; 3,285,995; 3,309,425; 3,434,981; 3,794,617 and Canadian Pat. No. 924,731.

SUMMARY OF THE INVENTION

This invention provides a composition of matter, polyester stabilized with a fire retardant amount of a reaction product of a phosphonitrilic halide and a halogenated monohydroxyaromatic compound crosslinked by a P—O—P bond.

The polyester may be saturated or unsaturated. Preferred materials are saturated, fiber-forming polyester condensation products of a diol and a dicarboxylic acid, or ester of such acid, selected from isophthalic acid, terephthalic acid and saturated aliphatic dibasic acids having 2 to about 10 carbon atoms.

The halogenated monohydroxy aromatic compounds used to make the phosphazenes may contain substituents other than hydroxy and halogen, and their exact nature is not critical. Preferably, they have an isolated benzene nucleus of up to about 12, more preferably up to about 10 carbon atoms. It is preferred that the phosphazene be derived from a halogenated phenol, preferably a brominated phenol such as the monobromodibromo-, and tribromophenols. Of these, p-bromophenol, 2,4-dibromophenol, and mixtures thereof are preferred.

In one embodiment, there is provided a composition of matter comprising (a) a fiber-forming polyester of a diol and a dicarboxylic acid selected from the class consisting of isophthalic acid, terephthalic acid and saturated aliphatic dibasic acids of 2 to about 10 carbon atoms, and (b) a fire retardant amount of a phosphazene crosslinked by a P—O—P bond, the crosslinked moieties having the formula

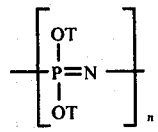

where n is 3 or more and T is a monohydroxy aromatic radical having the formula

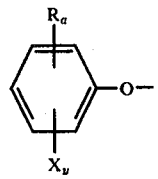

wherein R is an alkyl group of up to about 3 carbon atoms, $a$ is an integer of from 0-4 such that the number of carbon atoms in said aromatic compound does not exceed about 10, X is selected from chlorine and bromine, and $y$ is an integer of from 1-5.

For fiber-forming polyesters, we prefer to use phosphazene fire retardants having a melting point above about 200° C. More preferably, the melting point is from about 200° C. to about 300° C., most preferably about 280°-300° C.

The crosslinked phosphazenes can be made by (a) reacting a phosphonitrilic chloride with a sodium salt of the halogenated hydroxyaromatic compound, the amount of the sodium salt being less than that required to react with all the chlorine atoms in the phosphonitrilic chloride, (b) reacting the product thereby produced with a lower sodium alkoxide such that residual chlorine remains in the phosphazene, and (c) heating the phosphazene thereby produced to cause an increase in molecular weight.

Fire retardant polyester of this invention has a variety of uses. For example, the unsaturated polyesters can be used as structural materials on board ships and boats. Polyester fibers flame retarded according to this invention can be used to make protective clothing. The polyester fiber can be used alone or blended with other fibers such as cotton or wool. Films can be made from solutions or suspensions of the phosphazene fire retardants of high molecular weight provided herein.

In another embodiment we provide crosslinked phosphazenes. The crosslink is believed to be a P—O—P bond that links two phosphazene moieties. The phosphazene moieties are phosphazenes which are reaction products of a phosphonitrilic halide and a halogenated monohydroxyaromatic compound. The halogenated monohydroxyaromatic compound used to make the phosphazenes may contain substituents other than hydroxy and halogen, and their exact nature of structure is not critical. Preferably, they have an isolated benzene nucleus of up to 12, more preferably up to 10 carbon atoms. It is preferred that the phosphazene be derived from a halogenated phenol, preferably a brominated phenol having 1, 2, or 3 bromine atoms. Of these we prefer p-bromophenol, 2,4-dibromophenol, and mixtures thereof.

In a particular embodiment we provide as a new composition; a phosphazene crosslinked with a P—O—P bond; the crosslinked moieties of said phosphazene having rhe formula

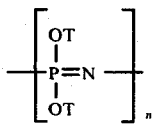

where n is 3 or more and T is a monohydroxy aromatic radical having the formula

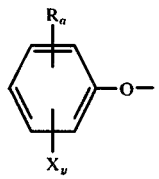

wherein R is an alkyl group of up to about 3 carbon atoms, a is an integer of value 0–4 such that the number of carbon atoms in said aromatic compound does not exceed about 10, X is selected from chlorine and bromine, and y is an integer of value 1–5.

DESCRIPTION OF PREFERRED EMBODIMENTS

As indicated above, a major aspect of this invention comprises use of phosphazenes as fire retardants for polyester.

Polyesters include linear and crosslinked polymers. The linear materials are prepared by reacting dibasic acids with glycols and are thermoplastic in nature. Typically, the glycol is ethylene glycol and the acid is isophthalic or terephthalic acid. Fibers can be spun from such materials and films can be made therefrom.

A larger group of polyesters is the unsaturated resins. These are used for reinforced shapes and coatings. For these resins, unsaturated acids or alcohols are incorporated in the polymer. By "unsaturated" is meant the presence of an active carbon-to-carbon double bond. Through this unsaturated bond, crosslinking is achieved. For example, if some of the phthalic acid in the polymer above is replaced by maleic acid, then crosslinking can be acheved using divinylbenzene or styrene. To achieve this crosslinking, a curing agent is mixed with the polymerizable mixture; typically, the curing agent is an organic peroxide.

Unsaturated polyesters of this type are called alkyl resins in the paint industry. They have many advantageous properties such as strength, weather resistance, pigmentability, etc.

As is well known, unsaturated polyester resins are based on prepolymers which are made by the esterification of dihydric alcohols with unsaturated and modifying dibasic acids and/or anhydrides. The unsaturated polymer is mixed with an unsaturated monomer, (e.g. styrene) with which is crosslinks. A catalyst, polymerization inhibitor and inert filler are among the typical additives; *Chemical Economics Handbook*, 580.1230E, Plastics and Resins, Stanford Research Institute (1969).

Polyester fibers are made by direct esterification, for example, reaction of terephthalic acid with ethylene glycol, or by transesterification. In the latter route, there is a catalyzed exchange of ethylene glycol for methyl groups, say of dimethyl terephthalate. The liberated methanol is removed by distillation to drive the exchange to completion. The 2-hydroxyethylenephthalate so-formed undergoes polycondensation, usually in the presence of a catalyst, to form the polymer. This may be broken into chips, blended, and remelted before spinning. Alternatively, the polymer can be made and continuously fed to spinnarets. *Chemical Economics Handbook, Fibers-Synthetic*, 543.4820G December, 1969, Stanford Research Institute, Menlo Park, Ca.

Polyester resins of the above types are well known in the prior art; confer for example, U.S. Pat. Nos. 2,909,501; 3,285,995; 3,309,425; 3,434,981; and Unsaturated Polyesters, Boenig, Elsevier Publishing Co., New York, N.Y. (1964). Descriptions of such resins in these works are incorporated by reference herein as if fully set forth. Some unsaturated resins which are articles of commerce, for example, the Glaskyd and Laminac Resins made available by American Cyanamid Company.

In a preferred embodiment, the polyesters are fiber-forming polymers, fibers and fabrics obtained by the reaction of glycols of the general formula $HO(-CH_2-)_xOH$ wherein x is an integer from about 2 to 10 with a dibasic acid. Such glycols include ethylene glycol, which is a preferred glycol, 1,3-propanediol, 1,5-pentanediol, 1,6-hexanediol, 1,7-heptanediol, 1,8-octanediol, 1,9-nonanediol, 1,10-decanediol or the like. These glycols, and particularly the preferred glycols ethylene glycol and 1,4-cyclohexanedimethanol, are reacted with dicarboxylic acids or suitable esters thereof, preferably terephthalic acid or dimethyl terephthalate, or other dibasic acids including isophthalic acid, adipic acid, sebacic acid, succinic acid, oxalic acid, glutaric acid, pimelic acid, suberic acid, azelaic acid and the like. In addition to being useful with polyesters derived from the more common diols and dicarboxylic acids the diol may be used as a reactive intermediate with other reactants including glycerol, sorbitol, pentaerythritol, methoxypolyethylene, glycol, neopentyl glycol, monohydroxypivalate, trimethylolpropane, trimesic acid, p,p'-dicarboxydiphenoxyethane, p-carboxyphenoxyacetic acid and the like.

In a more preferred embodiment the polyester fibers are derivatives of terephthalic acid such as poly(ethyleneterephthalate) or poly(1,4-cyclohexylenedimethyleneterephthalate).

Small aounts of other monomers may also be incorporated to alter one or more of the properties of the polyester. For example, small amounts of butanediol or isophthalic acid may be incorporated therein. Also, to improve the disperse dyeability of the polyester, small amounts of dibasic acids such as adipic acid, azelaic acid or dimer acids may be used. Sulfonated isophthalic acid may be employed to improve the basic dyeing properties of the polyester. In general, however, the amounts of these reactants should not exceed about 3 mol per cent of the polyester. Rather than modifying the polyester in this manner it may be more advantageous to enchance the desired properties thereof by blending the polyester with an amount of a suitable additive including other polyester or copolyester compositions. Polyester and copolyester fibers which may be treated effectively in accordance with the present invention include those described in U.S. Pat. Nos. 2,465,319 and 2.901,466. Such fiber-forming polyesters as described above have inherent viscosities usually greater than about 0.4.

Especially for use with polyester fibers, we prefer those phosphazenes of a halogenated phenol which have a melting point of above about 200° C. and about 300° C. A highly preferred melting point range is from about 280° to about 300° C.

Materials with the above melting characteristics, in general, can be readily admixed with molten polyester. Of course, one can use materials melting at other temperatures, if desired, especially if they are soluble in the polyester substrate at a temperature within about 200° to about 300° C.

Preferably, the fire retardant will not unduly decompose or volatilize at processing temperatures. In this regard, it is preferred that weight loss on heating be not substantially greater than the weight loss of the polyester substrate. In general, weight loss on heating should be about the same as the polyester substrate, although phosphazenes having a slightly greater weight loss can be used.

For fibers, color stability of the fire retardant is an important consideration. It is preferred that the fire retardant undergo little or no discoloration when heated under an inert gas at processing temperature for processing times. Thus, the fire retardant should not undergo discoloration to a desirable degree at 200°–300° C., while under nitrogen.

Fire retardant crosslinked phosphazenes for this invention preferably contain less than about 50 ppm $H_2O$ by weight and HBr and HCl concentrations should be less than 0.1 weight per cent.

The fire retardant should have some permanency in the fiber. In other words, the fire retardant phosphazene should be retained in the fabric to provide fire retardancy after laundering or dry cleaning. The degree of permanency desired will depend on the application of the fiber or fabric, as will be recognized by a skilled practitioner. Thus, to pass a Children's Sleep Wear Test (DOC FF 3-71) flammability protection must exist after 50 washings. Other applications do not require this high degree of permanency. For example, some drapery material applications require retention of the fire retardant for five or less dry cleanings.

Furthermore, the fire retardant should not render the fiber tacky. To avoid an undesirable degree of tackiness, the fiber must retain the fire retardant so that the fire retardant does not migrate to an undesirable extent to the polymeric fiber surface. To avoid an undesirable amount of this migration and to provide a desirable quantum of permanency in the fiber, it is preferred to use a crosslinked phosphazene having 4 or more

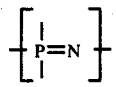

monomeric units. Preferably, the number of such units is high enough to provide a molecular weight of at least about 1500 and preferably at least 10,000 as set forth more fully below.

In accordance with this invention a fire retardant amount of condensation product of phosphonitrilic halide and a brominated phenol is admixed with a polyester of the type described above. The mixing can be accomplished by any technique known to a skilled practitioner. Thus, for example, the flame retardant agent can be thoroughly mixed with molten polymer before feeding to the spinnaret. In instances when it is desirable to lessen or minimize the time of exposure to high temperatures, it may be desirable to admix the fire retardant with the polyester very near (and downstream from) the spinnaret. Furthermore, the agent can be milled or molded with the resin, or blended with a prepolymer-unsaturated monomer mixture. In general, from about 2 to about 40 weight per cent or more additive is used. More preferably, from about 5 to about 30 weight per cent additive is employed and most preferably from about 10 to about 20 weight per cent.

As pointed out above, this invention comprises use of phosphazenes as flame retardants and the phosphazenes are derived from halogenated monohydroxy aromatic compounds. The exact nature or structure of the hydroxy aromatic compound is not critical and many of them are applicable in this invention. Of the applicable halogenated hydroxy aromatic compounds, certain are preferred. First of all, it is preferred that they be derivatives of bromine or chlorine. In other words, it is preferred that the halogenated hydroxy aromatics be a chloro compound or a bromo compound.

Secondly, it is preferred that the halogenated monohydroxy aromatic compound react without an untoward amount of difficulty with the phosphonitrilic halide. For this reason, it is preferred that the hydroxy aromatic be not too bulky so as to inhibit the reaction by steric hindrance. Likewise, it is preferred that groups adjacent to the hydroxy group should not interfere to an undesirable amount with the ability of the hydroxy group to react with a halogen atom in the phosphonitrilic halide.

With regard to the size of the hydroxy aromatic compound, it is preferred that it possess an isolated benzene nucleus. By this is meant preferred hydroxy aromatics are derived of benzene rather than naphthalene or some other fused ring system. An isolated benzene nucleus, for purposes of this invention, is a benzene ring which is not involved in a fused ring system. More preferably, the applicable halogenated aromatics with the isolated benzene nucleus are also devoid of substituents which hinder reaction to an undesirable extent. For this reason, and for their geater availability, it is preferred to use halogenated hydroxy aromatic compounds wherein the isolated benzene nucleus has up to 12, and more preferably up to 10, carbon atoms.

Furthermore, it is preferred that any substituents on the isolated benzene nucleus be comparatively small so as to avoid steric problems referred to above. For this reason, preferred substituents are lower alkyl such as alkyl groups of up to three carbon atoms. If such substituents are ortho to the hydroxy group, it is preferred that the groups to be primary rather than secondary or tertiary.

Another reason for preferring simple rather than complex halogenated aromatics is the fact that the halogen confers an appreciable amount of the fire retardancy property of the phosphazenes. For this reason, it is desirable that the amount of halogen, on a percentage basis, be rather high. In other words, all things considered, it is usually desirable not to 'dilute' the amount of halogen by having substituents which do not confer another useful property.

To achieve the desired balance of properties in the molecule, one may use a mixture of halogenated compounds to prepare the fire retardant phosphazene. For example, it is known that naphthalene compounds can be substituted with a comparatively high number of halogen atoms. Thus, it is suggested that one may use a halogenated naphthol together with a less complex material such as p-bromophenol to form a mixed phosphazene useful as a fire retardant for polyester.

Generally, because of their availability, we prefer that the halogenated hydroxy aromatic be a halogenated phenol. For purposes of this invention the term "halogenated phenol" shall mean a derivative of phenol, $C_6H_5OH$, in which one or more of the ring hydrogens is substituted with a halogen atom, preferably selected from chlorine and bromine. Of the halogenated phenols, we prefer the bromine compounds although the chlorine compounds are quite useful. Thus, to a great extent, the following description pertains to those aspects of the invention involving bromo compounds. However, it is to be understood that this is for purposes of brevity only, and the analogous chlorinated starting materials and phosphazenes derived from chlorinated hydroxy compounds, and polyesters containing same are also embodied within this invention. The bromophenols may be mono-, di- or tribromophenols; the chlorine analogs are also useful.

Applicable brominated and chlorinated hydroxy compounds are illustrated by those described by Formulas (I) and (II) above. Of those compounds, the ones which have up to two alkyl radicals bonded to the benzene ring are preferred. Because of their more ready availability, those having no alkyl groups or one alkyl group are more preferred.

As indicted above, the exact size and configuration of the organic group bonded to the benzene ring is not critical, and more heavily substituted phenols, e.g. those with more than three organic groups as well as those with groups having more than three carbons can be used, if desired. Use of phenols with halogenated side chains such as where R in Formula (I) is $-CH_2Br$ or $-CH_2CH_2Br$ is part of this invention.

Of the applicable halogenated hydroxyaromatics, the following are representative:
 a. o-bromophenol
 b. p-bromophenol
 c. 2,6-dibromophenol
 d. 2-methyl-4-bromophenol
 e. 2-methyl-4,6-dibromophenol
 f. 2-ethyl-4-bromophenol
 g. 2-ethyl-4,6-dibromophenol
 h. 4-methyl-2-bromophenol
 i. 2,6-dimethyl-4-bromophenol
 j. 2-methyl-3,4,5,6-tetrabromophenol
 k. pentabromophenol
 l. 2,6-diethyl-p-bromophenol
 m. 2,4,6-trimethyl-2-bromophenol
 n. 2,4,6-tribromophenol
 o. 2,3,5,6-tetramethyl-4-bromophenol The phosphonitrilic halide starting materials for this invention can be phosphonitrilic chloride $(PNCl_2)_n$ or phosphonitrilic bromide $(PNBr_2)_n$ where $n$ is 3 or greater. Because of their more ready availability, the phosphonitrilic chlorides are preferred.

Phosphonitrilic chlorides used to prepare the phosphazene fire retardants can be produced by
 a. Reacting $PCl_5$ with ammonium chloride; U.S. Pat. No. 3,367,750,
 b. reacting $PCl_5$ with ammonia, U.S. Pat. No. 3,656,916,
 c. reacting ammonia with phosphorus with chlorine, U.S. Pat. No. 3,658,487,
 d. reacting phosphorus trichloride, chlorine and ammonium chloride; U.S. Pat. No. 3,359,080, and
 e. reaction of ammonium chloride and $PCl_5$ in the presence of certain metal salts; U.S. Pat. Nos. 3,407,047; 3,462,247 and German Pat. No. 2,321,221.

Other known procedures for producing phosphonitrilic halides are found in Am. Chem. J. 19, 728 (1897), Berichte, 57B, 1343 (1924), U.S. Pat. Nos. 2,788,286; 3,008,799; 3,249,397; 3,347,643; 3,372,005; 3,378,353; 3,379,511 and Netherlands Pat. No. 70/05128.

The procedures of the aforementioned patents and publications are incorporated by reference herein as if fully set forth.

It is known that the molecular weight of linear $PNCl_2$ can be increased by heating under a blanket of nitrogen; James M. Maselli et al, *Phosphonitrilic Laminating Resins*, Technical Report AFML-65-314 June (1965), prepared by the Research Division of W. R. Grace and Company, Clarksville, Maryland under USAF Contract No. AF 33(615)-1640; AD 815233. Thus, as set forth on page 47 of that report, a sample of $PNCl_2$ with a molecular weight of 700 by vapor phase osmometry and prepared by the procedure described in Section II (Part A.1) of the report was placed in a resin kettle fitted with a nitrogen inlet stirrer and exhaust tube condenser. The resin kettle was heated to 250° ± 10° C. for a total of 55 hours while the polymeric $(PNCl_2)$ was stirred under a blanket of dry nitrogen. Samples of the polymer were taken at selected intervals of time during the heating for molecular weight determination. The data given are as follows:

| Time (hours) | Molecular Weight (VPO) |
|---|---|
| Start | 700 |
| 10 | 1200 |
| 40 | 3200 |
| 55 | 6900 |

Such compositions can be used as starting materials for this invention. When heating was continued for an additional 8 hours at temperatures in excess of 250° C. the viscous, soluble oil (m. wt. 6900) was converted to the familiar insoluble "inorganic rubber".

It is also known that poly(dichlorophosphazene) can be prepared by polymerization of cyclic trimer to yield a product having molecular weights in the range of 1 × $10^6$ to 2 × $10^6$; confer Allcock, *Phosphorus-Nitrogen Compounds*, Academic Press, N.Y. (1972) pages 309–310, 346–352. These compositions can be used as starting materials for this invention.

Furthermore, it is known that cyclic phosphonitrilic chlorides are soluble in solvents such as ligroin while linears are not; Audrieth et al, *Chem. Rev.* 32, 111–127 (1943). The solvent-cyclic freaction can be separated from the linears and subjected to further treatment to separate out cyclic trimer. For example, the solution with the cyclics can be heated to 150°–190° C. at about 60 mm. Hg while passing vaporized heptane through the solution. This procedure removes cyclic trimer. The residue from which the trimer is removed contains other cyclics, e.g. $(PNCl_2)_4$, $(PNCl_2)_5$, $(PNCl_2)_6$, $(PNCl_2)_7$ and may also contain higher cyclic oligomers. Such mixtures can be used to prepare halophosphazenes of this invention.

The phosphonitrilic halide starting material can be linear, cyclic, or mixtures of these. In general, processes for producing phosphonitrilic halides provide a crude mixture containing from 50 or less to about 95 weight per cent cyclic materials and the remainder linears. Although pure cyclic and linear isomers can be separated and used as the starting materials of this invention, the cyclic and linear mixed isomers are satisfactory and preferred because of their cheaper, more practical processes of production. The mixed cyclic and linear isomers of phosphonitrilic halide are generally oily, viscous liquids, although the pure materials may be solid under normal ambient conditions.

In a preferred embodiment the products of this invention are made from compositions having 65–75 per cent cyclic phosphonitrile chloride polymers and 35–25 per cent linear materials. In these starting materials, the cyclic distribution ranges from 60–75 per cent trimer, 18–24 per cent tetramer, and 7–12 per cent of pentamer. Other preferred starting materials have cyclic contents ranging from 80–85 per cent cyclic up to 95 or 100 per cent cyclics.

Thus, in a more preferred embodiment, the phosphonitrilic chloride starting material is a mixture within the following composition range:

|  | Weight per cent |
| --- | --- |
| Cyclic trimer | 35–85 |
| Cyclic tetramer | 20–8 |
| Cyclic pentamer | 12–4 |
| Cyclic hexamer | 7–1 |
| Cylic heptamer | 6–0 |
| Linears and higher cyclics | 20–2 |

To prepare halogen substituted, hydroxyaromatic phosphazenes, the phosphonitrilic halides describe above may be reacted with metal derivatives of the phenols. Of the metals, the alkali metals are preferred. Sodium and potassium are highly preferred because of their availability, and sodium is most preferred because of its reactivity and relative inexpensiveness. The metal derivative is prepared by reacting the metal with the phenol in any convenient manner. For example, sodium can be reacted with a p-bromophenol using an inert hydrocarbon such as benzene or p-dioxane or tetrahydrofuran as a reaction mixture. The sodium may be in the solid state or may preferably be melted by heating to about 100° C. When using molten sodium, it is convenient to employ a reaction medium which has a boiling point above the solidification temperature of the sodium. Toluene, kerosene, or No. 9 oil or p-dioxane can be employed. Kerosene or No. 9 oil may be somewhat difficult to remove from the product, and accordingly, toluene is a reaction medium of choice.

It is convenient to use an excess of the phenol as a precaution against unreacted sodium. Good results are obtained utilizing a 1–10 weight per cent excess. However, greater or lesser excesses can be used.

The alkali metal derivative of the brominated phenol is reacted with the phosphonitrilic halide. This can be accomplished by admixing the phosphonitrilic halide with the mixture of alkali metal derivative, solvent and excess phenol prepared as described above. Typical solvents which can be employed are p-dioxane and tetrahydrofuran.

In many instances, the reaction is rapid and exothermic at the beginning and requires no heating. After mixture of the reactants is complete, it may be convenient to heat the resultant reaction mass and hold it at reflux temperature for such time as analysis indicates complete reaction. Reaction times in the range of from ½ to 20 hours can be used. This is somewhat dependent upon the reaction temperature which is usually within the range of from ambient to 110° C.; more preferably from about 55° to about 110° C.

After conduction of the reaction, the excess free hydroxy compound and the solvent are removed by distillation or other suitable means. These can be recycled for later use.

As with the preparation of the metal derivative of the hydroxy compound, the phosphazene synthesis proceeds well at ambient pressure. Accordingly, atmospheric pressure is of choice. However, greater or lesser pressures can be used if desired.

When preparing mixed phosphazenes, the phosphonitrilic halide is reacted with a mixture of metal derivatives of two or more phenols. Thus, for example, one can prepare mixed phosphonitrilic halide condensation products by reacting the sodium derivative of a mixture of 2-bromophenol and 2,6-dibromophenol.

One can prepare the phosphonitrilic halide condensation products by reacting the brominated phenol and/or the lower alkanol with the phosphonitrilic halide in the presence of a tertiary amine such as pyridine. In this regard, one may use the method set forth in Netherlands Pat. No. 71/06772.

This affords a milder technique which can be used in those instances where there may be appreciable attack of a bromine substituent by alkali metal.

Alternatively, one can prepare the metal bromophenoxy derivative by reacting the bromophenol with the corresponding metal hydroxide. Reaction conditions similar to those described above for use with the alkali metal can be used.

As explained more fully below, crosslinking and formation of a P—O—P bond can be achieved by heating a phosphazene to split out by-product, organic halide. The organic halide may be derived from an aryloxy group on the phosphazene.

However, in many instances it is easier to achieve reaction by splitting out an alkyl halide or alkyl ether. Accordingly, in a preferred embodiment of this invention the intermediate phosphazene is prepared by reacting less than a stoichiometric amount of desired halogenated hydroxyaromatic compound with the phosphonitrilic halide starting material. Prior to reaction with the aryloxy compound, or thereafter, or contemporaneously the remaining halogens in the phosphonitrilic halide are reacted to become substituted with lower alkoxy groups. These, upon heating, react with residual halogen (or two alkoxy groups react) to split out the corresponding lower alkyl halide (or alkyl ether), thereby achieving crosslinking and formation of a P—O—P bond.

When a lower alkoxy group is formed in the preparative process the amount thereof is not critical. It is dependent to some extent on the desired amount of halogenated hydroxyaromatic compound as well as the desired amount of crosslinking. Generally, one may employ from about 1 to about 0.5 theory of halogenated hydroxyaromatic compound for purpose of this invention. One theory is the amount of halogenated hydroxyaromatic compound (or derivative thereof) theoretically required to react with all of the halogen atoms in the phosphonitrilic halide starting material. In other words, 1 theory is equal to the stoichiometric amount. Although the above range is preferred, it is to be understood that greater or lesser amounts can be employed. Greater amounts can be employed since ordinarily, even with a large excess of halogenated hydroxyaromatic compound, some residual halogen remains in the phosphonitrilic chloride.

If less than a theory of halogenated hydroxyaromatic compound is utilized, one then usually employs enough alkoxy compound or derivative thereof to theoretically react with all of the remaining halogens or a portion thereof. The lower alkoxy compound generally contains up to about 6 carbon atoms with those having up to about 3 being preferred. A preferred material is propanol or a derivative thereof such as sodium propoxide.

Usually, even when 1 theory of hydroxyaromatic or 1 theory of hydroxyaromatic plus lower alkoxy compound is employed some residual halogens still remain in the intermediate product phosphazene. The reason for this is not entirely clear, but evidently some of the halogen atoms are more difficult to substitute than others. Usually the number of residual halogens is sufficient to afford the desired amount of crosslinking by the heating step to be discussed below. If a greater amount of crosslinking is desired, then one can use less than a theory of hydroxyaromatic or (hydroxyaromatic plus lower alkoxy) compound to ensure the presence of a greater amount of halogens.

To prepare the crosslinked product, one heats the phosphonitrilic intermediate to cause P—O—P bond formation to take place. During the heating, gas may be evolved. This gas may be by-product organic halide derived from (a) the organic radical in the phenolic or alcoholic residue bonded to phosphorous in the phosphazene as discussed above, and (b) the halogen remaining after treatment with the alcohol, phenol, or metal derivative of these substances. Although not bound by any theory, it is believed the product produced by the heating step can be illustrated by the following formula depicting a portion of two chains being bridged by —P—O—P bonds formed upon heating. Such bonds can be formed, as mentioned above, by splitting out a halide, or by splitting out an ether by-product.

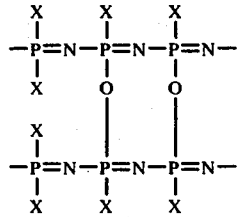

It is to be understood that the above formula is not limiting; similar structures could be formed between rings or between a ring and a chain. Likewise, the bridging oxygens need not be on adjacent phosphorus atoms and some of the groups indicated by X can be halogen or alkoxy or all of them can be halogenated aryloxy. Likewise, if some of the groups represented by X are halogen, they could be available for further crosslinking with another, or the same, ring or chain.

The temperatures to which the intermediate product is heated, is not critical. It is desired that the temperature be high enough to afford reaction, but not so high as to cause undue decomposition of product or reactant. In general, mildly elevated temperatures are employed and the temperature is usually higher than that used to react alcohol, phenol, alcoholate, or phenolate with phosphonitrilic halide. Good results are achieved if the temperature is within the range of from about 100° to about 220° C.; higher and lower temperatures can be used. A preferred temerature range is from about 130° C. to about 190° C.

The heating time is not critical. The time is at least somewhat dependent upon the inherent ability of the product of the reaction step to achieve reaction. Also, the time is dependent on the degree of reaction desired. In general, longer heating times, as higher heating temperatures, afford greater amount of crosslinking, increases. Hence, one may use a higher temperature and shorter heating period and achieve a degree of reaction similar or the same as that achieved by using a lower temperature and longer heating time. Thus, with a minor amount of simple experimentation, a skilled practitioner can readily determine what time and temperature to be employed to achieve the desired amount of reaction. In general, heating times of from about 178 to about 60 minutes afford good results. A preferred time range is from about 3 to about 30 minutes. However, times as long as three hours or more can be used.

The heating step can be conducted in the presence of an inert, liquid reaction medium such as toluene, heptane or other hydrocarbon, but it is unnecessary to do so. Likewise, it is unnecessary to conduct the step on a single, purified compound. For economic reasons, it is preferred to conduct the process on the intermediate phosphazene prepared from a mixture of phosphonitrilic halides. If desired, the crosslinking step can be conducted in the presence of an inert atmosphere, but it is unnecessary to do so. Nitrogen, neon, or other inert gas can be used.

The heating step can be conducted at ambient pressure. However, subatmospheric and superatomospheric pressure can be used if desired, for the process pressure is not critical. If elevated pressures are selected, they should not be so high as to unduly impede the process by hampering evolution of by-product.

It is preferred that the crosslinked product have a molecular weight of from about 1,500 to about $2 \times 10^7$, or higher. With regard to the very high molecular weight materials these can be made by crosslinking phosphazenes of very high molecular weight prepared from phosphonitrilic halides, discussed by Allcock, pages 309–310, 346–352, supra. Preferably, the molecular weight of crosslinked product is from about 3000 to about 1,000,000 and more preferably from about 10,000 to about 100,000.

For materials having a molecular weight of up to 20,000 the number average molecular weight can be determined by vapor phase osmometry. For those materials of molecular weight of from about 10,000–1,000,000, the number average molecular weight can be determined by membrane osmometry. For materials of molecular weight of up to 5,000,000 weight average molecular weight can be determined by light scattering photometry.

It is to be understood that the halogenated hydroxyaromatic phosphazene fire retardants, even after crosslinking, may contain a minor amount of residual halogen resulting from incomplete substitution of the halogen atoms in the phosphonitrilic halide with hydroxyaromatic compound. It is preferred that the amount of residual halogen be at a level as low as convenient; preferably the amount of residual halogen is less than 2 weight per cent, or more preferably less than 1.0 weight per cent.

This invention can be extended to preparation of P—O—P bonded phosphazenes made by other techniques. For example, instead of splitting out an organic halide from a partially substituted phosphonitrilic chloride as described above, one can
  a. react a mixture of (i) phosphonitrilic chloride and (ii) a fully or substantially fully substituted organophosphazene, or
  b. a mixture of (i) a fully or substantially fully substituted organophosphazene and (ii) a partially substituted organophosphazene.

As with the splitting out of an organic halide from a partially substituted organophosphazene, for best results with (a) and (d), the reaction mixture contains from about 2–20 weight per cent chlorine; it being understood that chlorine-richer or leaner mixtures can be used.

Reaction temperatures are generally between 120° and 220° C., preferably 130°–190° C. Ambient pressures, super-or subatmospheric pressures can be used; pressure being non-critical. Preferred subatmospheric pressures are 5–200 mm Hg. Reaction times of 0.5 to 3 hours can be used. Longer times, say up to 48 hours or more, can be used. An inert gas atmosphere is non-critical but a nitrogen or argon atmosphere, for example, can be used if desired.

EXAMPLE 1

A solution of 135.5 (0.78 mole) of p-bromophenol (97 per cent, freshly distilled) in 150 ml of tetrahydrofuran (THF) was added dropwise over a period of 40 minutes to a suspension of 17.9 g (0.77 mole) of sodium in 250 ml of THF while refluxing. Continuation of reflux (69° C.) for 8 hours was used to assist formation of sodium p-bromophenoxide.

A 50.1 g (0.43 mole) $(PNCl_2)_{3,4,5}$ sample with linears removed by heptane extraction (VPC analysis: 67.4 per cent trimer, 10.6 per cent tetramer, 3.9 per cent pentamer) was dissolved in 100 ml of THF. This solution was added dropwise over a 90 minute period to the sodium p-bromophenoxide slurry maintaining the reaction temperature at 25° C. with an ice bath. The mixture was held at reflux for a total of eight hours.

Then, while refluxing the reaction mixture, a solution of sodium propoxide (0.17 mole) was added dropwise over a 20 minute period. The reaction mixture was refluxed for 2 more hours.

The reaction mixture was stripped of THF on a rotary evaporator at full vacuum and 50° C. to get a paste-like solid. This product was heated to 180° C. under full vacuum and held at this temperature for 2 hours.

The product was dissolved in 500 ml of chloroform and washed with 5 per cent NaOH (2 × 200 ml) and finally washed with water (2 × 200 ml). The organic layer was dried over anhydrous $Na_2SO_x$ and then filtered to obtain a clear amber solution. The solvent was removed by stripping on a rotary evaporator at 80° C. and full vacuum. The product crystallized to a light cream colored solid and weighed 146 grams.

In an attempt to reduce the chlorine content the above product was heated to 160° C. on a rotary evaporator at full vacuum and further stripped for 2 hours. This resulted in a 2.4 per cent weight loss.

The VPC analysis for the starting phosphonitrilic chloride given above is complete as to the entire composition since the method employed differentiates $(PNCl_2)_3$, $(PNCl_2)_4$, $(PNCl_2)_5$, $(PNCl_2)_6$, and $(PNCl_2)_7$ but does not differentiate the higher cyclics.

The procedure of this example is widely applicable to crosslink phosphazenes of halogenated monohydroxy aromatic compounds with the backbond

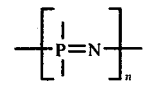

where $n$ is 3 or greater. Cyclics, linears and mixtures thereof can be employed as starting materials. The value of $n$ can be 3, 10, 100, 500, 1000, 5000 or 10,000 or more.

Similar results are obtained when 2,4-dibromophenol, or the compounds designated (a) and (c) through (o) above are substituted for the p-bromophenol. Similar results are obtained using a mixture of 2,4-dibromophenol and p-bromophenol. Preferredd mixtures have from 0.5 to 10 weight per cent dibromophenol, preferably from 2–5 weight per cent 2,4-dibromophenol.

Similar results are obtained when
  a. one theory of p-bromophenol sodium salt is followed with 0.5, or 0.2, or 0.1 theory of sodium propoxide.
  b. 0.95 theory of p-bromophenol sodium salt is followed by 0.5 or 0.05 theory of sodium propoxide,
  c. 0.75 theory of p-bromophenol sodium salt is followed by 0.5, or 0.25 or 0.05 theory of sodium propoxide.

Similar results are obtained when the crosslinking step is conducted between 120° and 220° C. for 0.5 to 48 hours. Similar results are obtained at 0.01 mm Hg pressure to ambient pressure during the heating step.

EXAMPLE 2

Three 500 ml three-necked flasks were each charged with 100 ml of pyridine and 50.0 g (0.432 mole) of heptane-extracted decolorized (activated carbon) phosphonitrilic chloride (VPC anal. 65.5 per cent trimer, 10.3 per cent tetramer, 4.2 per cent pentamer, 1.2 per cent hexamer). A solution of bromophenol (91.8 per cent para:, 8.0 per cent 2,4-dibromophenol) in 50 ml of pyridine wa added to each phosphonitrilic chloride solution over a period of 30 minutes at a pot temperature of 40°–50° C. A 149.5 g (0.864 mole) sample of bromophenol was used for reaction 1, 142.0 g (0.820 mole) for reaction 2, and 134.5 g (0.778 mole) for reaction 3. The reaction mixtures were heated at reflux (~116° C.) for 6 hours and then allowed to stand at room temperature overnight. Reaction 1 was treated with 5.2 g (0.0864 mole) of 1-propanol, reaction 2 with 7.8 g (0.130 mole) of 1-propanol, and reaction 3 with 10.4 g (0.173 mole) of 1-propanol. The reaction mixtures were heated at 50° C. for 3 hours and then refluxed (~116° C.) for 4 hours. Reactions 2 and 3 were given an additional 5 hours reflux.

Each reaction mixture was treated with 150 ml of chlorobenzene and enough 16 per cent NaOH solution was added (~115 ml) to give an aqueous phase with a pH of 8. The organic layer was then drawn off and washed with 75 ml of water. The solvent was stripped from the organic phase at 80° C./1 mm Hg using a rotary evaporator to give the crude product as a viscous, highly colored oil. Reaction 1 gave 174.3 g of product, reaction 2 gave 160.5 g, and reaction 3 gave 143.8 g.

The oils were each dissolved in 500 ml of solvent (reaction 1 in toluene, reaction 2 in chlorobenzene and reaction 3 in chloroform). The solutions were washed with 5 percent NaOH (2 × 3 ml) and water (2 × 300 ml). Emulsions were encountered inn some of the water washes. Neutralization of the aqueous phase withh dilute HCl helped break the emulsions. The organic phases were then dried over 23 g of anhydrous MgSO$_4$, and 3.5 g of activated carbon (Nuchar C-115-N) was added to each to reduce the color. The solutions were filtered through a bed off celite and stripped of solvent at 80° C./1 mm Hg using a rotary evaporator. Reaction 1 gave 130.8 g of a dark brown glass. Reaction 2 gave 124.0 g of a yellow glass, and reaction 3 gave 108.2 g of a yellow glass.

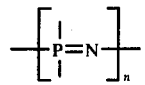

$n$ is 3 or greater. Cyclics, linears and mixtures thereof can be employed as starting materials. The value of $n$ can be 3, 10, 100, 500, 1000, 5000, or 10,000 or more.

Similar results are obtained when 2,4-dibromophenol, or the compounds designated (a) and (c) through (o) above are substituted for the p-bromophenol. Similar results are obtained using a mixture of 2,4-dibromophenol and p-bromophenol. Preferred mixtures have from 0.5 to 10 weight per cent dibromophenol, preferably from 2–5 weight per cent 2,4-

Summary of Product Analyses

| Reaction | Product Color | Product wt (g) | Cl Wt. per cent | Bromophenol (ppm) | No. Ave. Mol Wt. |
|---|---|---|---|---|---|
| 1 | Dark brown | 130.8 | 0.16 | 1270 | 2850 |
| 2 | Yellow | 124.0 | 0.51 | 370 | 3320 |
| 3 | Yellow | 108.2 | 0.52 | 500 | 3870 |

The above example illustrates a preferred employment of this invention for forming P—O—P bonded phosphazenes. In this embodiment the starting phosphonitrilic halide is reacted with the hydroxy compound or compounds in the presence of a hydrogen halide acceptor. By carrying out the reaction in the presence of an acid acceptor the hydrogen halide by-product is complexed and is removed from the reaction mixture. A suitable acid acceptor is one capable of complexing with and removing the hydrogen halide produced, say, by precipitation. In general, the tertiary amines are suitable hydrogen halide acceptors. Typical materials are tripropylamine, triethylamine, pyridine, piperidine and the picolines. Pyridine is preferred because it may also have a catalytic effect on preparation of P—O—P bonds. Preferably one employs more than the theoretical amount of acid acceptor necessary to complex with the hydrogen halide formed. In general, from about two to about three or more times the weight of the phosphonitrilic halide is employed. Theoretically one stoichiometric amount of acid acceptor would be all that is required. More than that is used, however, in order to facilitate rapid fixation of the hydrogen halide by-product and to give a relatively fluid reaction mixture. There is no real upper limit on the amount of acid acceptor employed and this is governed by such secondary characteristics as economics and size of the reaction vessel. For example, one may use up to 10 to 100 times the weight of phosphonitrilic halide used in the reaction mixture.

Similar results are obtained when the heating step is conducted for 0.5 to 48 hours.

As with the other example, the VPC analysis given is incomplete. The unreported fraction is essentially higher cyclics.

The procedure of this example is widely applicable to crosslink phosphazenes of halogenated monohydroxy aromatic compounds with the backbone dibromophenol.

Similar results are obtained when
a. one theory of p-bromophenol is followed with 0.5, or 0.2, or 0.1 theory of 1-propanol,
b. 0.95 theory of p-bromophenol is followed by 0.5 or 0.05 theory of 1-propanol,
c. 0.75 theory of p-bromophenol is followed by 0.5 or 0.25 or 0.05 theory of 1-propanol.

Similar results are obtained when the reaction is conducted between 120° and 220° C. for 0.5 to 48 hours. Similar results are obtained at 0.01 mm Hg pressure to ambient pressure during the heating step reaction.

The products of the above examples are incorporated in poly(ethylene terephthalate) and poly(1,4-cyclohexylmethyleneterephthalate) so that the flame retardant concentration is from 2 to 40 weight per cent. The treated polyester can be utilized to prepare flame retardant polyester fabric. The fire retardant polyester fiber can be blended with cotton or wool. For example, a blend of 65/35 (polyester/cotton), 50/50 (polyester/cotton) and 80/20 (polyester/cotton) can be prepared. Likewise, a mixture of 55/45 polyester/wool can be used. Such fabrics can be used to prepared clothing. Likewise, the mixture of equal parts polyester and cotton can be employed to prepare sheets and pillow cases. Preferably, the molecular weight of phosphazene in the polyester is from about 1500 to about $2 \times 10^7$.

As another example, additional experiments were conducted to prepare crosslinked phosphazenes. A sodium salt of p-bromo-phenol was prepared in p-dioxane using an excess of the phenol. A phosphonitrilic chloride preparation (98 per cent trimer, 2 weight per cent tetramer) in dioxane was added to the salt. Approximately ½ of the dioxane was removed (by distillation) and replaced with pyridine. The resultant mixture was refluxed for 15 hours.

The product was isolated in a manner analogous to that reported in the above examples. The number average molecular weight of two products prepared by this method were 1260 and 1390 even with residual chloride values of 1.6 and 1.3 weight per cent, respectively, while the theoretical molecular weight of pure trimeric product would be 1167.

Also, the fire retardants of this invention may be applied to the surface of the polyester to be treated. This can be done by contacting the fire retardant, or a solution, emulsion, dispersion, or suspension thereof, with the substrate by spraying, dipping, spreading, rolling or similar technique such as use of a textile pad bath. If a solution or suspension or similar mixtures of fire retardant and solvent is used, the product is further treated with heat to evaporate the solvent or solvents employed. Prior to this the treated material can be treated to remove excess liquid by squeezing, centrifuging, pressing, or other operations.

Treatment of the surface can efficaciously be conducted, for example, using a polyester film, fiber, thread, cloth, or garment. In general, it is desirable to deposit enough fire retardant so that the percentage concentration thereof is 2–40 weight per cent, preferably, 2–30 weight per cent, and more preferably 10–20 weight per cent.

The P—O—P crosslinked condensation products of phosphonitrilic dihalide (chloride or bromide) and brominated phenol can be used to flame retard other materials such as polystyrene, polyvinyl chloride, polyurethane, polycarbonate, polyamide, and epoxy resin.

For polystyrene, molding powders or expandable beads can be prepared. In addition, the surface of an expandable bead can be impregnated with mixtures of the fire retardant additive and organic media such as propanol, methanol, toluene, etc. and then dried.

As to polymers suggested, reference is made to Floyd, *Polyamide Resins* (1958); Skeist, *Epoxy Resins* (1958); Dombrow, *Polyurethanes* (1958); and Christopher and Fox, *Polycarbonates*, all published by Reinhold Publishing Corp., New York, N.Y. Polymer compositions disclosed therein are incorporated by reference herein as if fully set forth. To illustrate this portion of the invention the following compositions which may be treated with from 2 to 40 weight per cent of a bromophenoxyphosphazene prepared from any of the PNCl$_2$ compositions set forth in Tables 1–5 of Emsley, supra.

| Polystyrene molding powder | |
|---|---|
| Styrene | 10,000 parts (by weight) |
| Barium sulfate | 100 parts |
| Benzoyl peroxide | 25 parts |
| Water | 20,000 parts |
| Polystyrene expandable bead | |
| Styrene | 20,000 parts |
| Sodium pyrophosphate | 2 parts |
| Hexane | 1,500 parts |
| Benzoyl peroxide | 70 parts |
| Water | 20,000 parts |
| Protective colloid | 70 parts |
| PVC composition | |
| Polyvinyl chloride | 100 parts |
| Dioctyl phthalate | 40–45 parts |
| Tin stabilizer | 9 parts |

In addition, epoxy resins, polyamides, and polycarbonates disclosed in the above-cited books can be treated with 2 to 40 weight per cent of a phosphazene additive of this invention.

We claim:
1. As a composition of matter, a halogenated monohydroxy aromatic phosphazene crosslinked by a P—O—P bond, said phosphazene being prepared by a process comprising:
  a. reacting a phosphonitrilic chloride with a sodium salt of a monohydroxy halogenated phenol, the amount of said salt being less than that required to react with all the chlorine atoms in said phosphonitrilic chloride, said amount of said salt being from about 1 to about 0.5 theory,
  b. reacting the product thereby produced with a lower sodium alkoxide such that residual chlorine remains in the intermediate thereby produced, the amount of said lower alkoxide being enough to theoretically react with all of the remaining chlorine atoms in said phosphonitrilic chloride, and
  c. heating said product thereby produced to a temperature of 120°–220° C. for 0.5–48 hours.
2. A composition of claim 1 having a melting point above about 200° C.
3. A composition of claim 1 wherein said halogenated monohydroxyaromatic phosphazene is a phosphazene derived from p-bromophenol or 2,4-dibromophenol, or mixtures thereof.

* * * * *